United States Patent [19]

Ibbotson

[11] 4,085,140
[45] Apr. 18, 1978

[54] CARBODIIMIDES

[75] Inventor: Arthur Ibbotson, Manchester, England

[73] Assignee: Imperial Chemical Industries Limited, United Kingdom

[21] Appl. No.: 827,097

[22] Filed: Aug. 23, 1977

[30] Foreign Application Priority Data

Sep. 22, 1976 United Kingdom ............... 39266/76

[51] Int. Cl.$^2$ ......................................... C07C 119/055
[52] U.S. Cl. .............................................. 260/566 R
[58] Field of Search ..................... 260/566 R, 551 CD

[56] References Cited

U.S. PATENT DOCUMENTS 4,014,935  3/1977  Ibbotson ........................... 260/566 R Primary Examiner—Gerald A. Schwartz
Attorney, Agent, or Firm—Cushman, Darby & Cushman

[57] ABSTRACT

A process for the conversion of isocyanate groups to carbodiimide groups which comprises contacting the compound containing the isocyanate groups with a cyclic phosphorus compound which catalyses said conversion in the presence of a nitrogeneous base and the use of the products thereof in the manufacture of isocyanate-based polymers.

6 Claims, No Drawings

CARBODIIMIDES

This invention relates to a process for the conversion of isocyanate groups to carbodiimide groups in the presence of catalysts for that conversion and in the presence of a nitrogeneous base The process can be applied to both monoisocyanates and polyisocyanates and in the case of the latter the invention also relates to the production of isocyanate based polymers from the products of the present process.

The conversion of isocyanate groups to carbodiimide groups under the influence of a wide variety of catalysts, in particular cyclic phosphorus containing catalysts is known. When, as is the case with isocyanates prepared by the phosgenation route, the isocyanate contains traces of acidic substances, conversion of isocyanate groups to carbodiimide groups with such catalysts is inhibited and the use of certain acid acceptors to overcome this problem has been proposed in our British Pat. No. 1,476,088 We have now found that if the conversion process is carried out in the presence of a nitrogeneous base the rate of reaction is increased and the reaction can be satisfactorily extended to isocyanates which have quite high acid values.

Thus, according to the present invention, there is provided a process for the conversion of isocyanate groups to carbodiimide groups which comprises contacting the compound containing the isocyanate groups with a cyclic phosphorus compound which catalyses said conversion, in the presence of a nitrogeneous base.

The process of the invention may be applied to any compound containing isocyanate groups including, for example, organic isocyanates, inorganic isocyanates and acyl isocyanates.

Examples of such isocyanate group-containing compounds include organic isocyanates such as phenyl isocyanate, o, m and p-tolyl isocyanates, p-chlorophenyl isocyanate, naphthyl isocyanate, tolylene-2,4- and -2,6-diisocyanates and mixtures thereof, p-phenylene diisocyanate, chlorophenylene-2,4-diisocyanate, hexamethylene diisocyanate, 4,4′-diphenylmethane diisocyanate and 2,4′-diphenylmethane diisocyanate and mixtures of such isomers and other isomeric diphenylmethane diisocyanates. The process may also be applied to crude mixtures of polyisocyanates, for example the mixtures of methylene bridged polyphenyl polyisocyanates obtained by phosgenation of polyamine mixtures produced by the condensation of aniline and formaldehyde in the presence of a catalyst. A large variety of such polyisocyanate mixtures of varying composition in respect of diisocyanate and higher functionality polyisocyanate content are known and have been described in the art. The present process may be applied to any of these mixtures or to any of the mixtures of methylene bridged polyphenyl polyisocyanates which are available commercially.

The present process is particularly useful when applied to aromatic polyisocyanates, i.e. those having two or more isocyanate groups. Examples of such polyisocyanates include tolylene diisocyanate and the commercially available mixtures of the isomers thereof, diphenylmethane diisocyanates and the mixtures of methylene bridged polyphenyl polyisocyanates referred to above. The process is especially valuable for use with mixtures of methylene bridged polyphenyl polyisocyanates.

The application of the present process could result in the conversion of all the isocyanate groups in an isocyanate to carbodiimide groups, the process however has been found particularly useful for the conversion of only a proportion of the isocyanate groups. In the case of diisocyanates and higher polyisocyanates the process is valuable for the conversion of from 3% to 35% of the isocyanate groups to carbodiimide groups. This use of the present process is of value for introducing into the isocyanate, uretonimine groups which are formed as adducts of a carbodiimide group and an isocyanate group.

Uretonimine groups are produced by reacting an isocyanate group with a carbodiimide group and may be easily introduced into an isocyanate composition by converting some of the isocyanate groups to carbodiimide groups by the present process and then allowing the carbodiimide groups to react with unreacted isocyanate groups to form uretonimine groups.

Formation of a uretonimine takes place as follows:

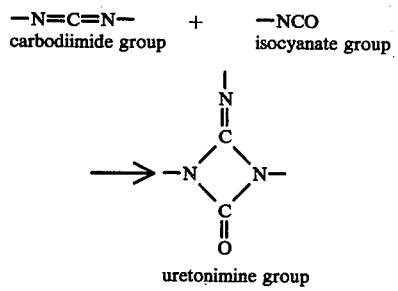

uretonimine group

The reaction is reversible and the adduct tends to split into carbodiimide and isocyanate on heating to elevated temperature.

Once carbodiimide groups have been introduced into an isocyanate composition, reaction between carbodiimide groups and isocyanate groups takes place with formation of uretonimine groups.

In order to permit this reaction to proceed to near completion it is normally necessary to allow the isocyanate/carbodiimide reaction mixture to stand for a time at room temperature for the uretonimine-forming reaction to take place. Conversion to uretonimine may not go to absolute completion and there sometimes remains in the composition a small amount of carbodiimide which is not converted to uretonimine despite the presence of excess isocyanate groups.

Thus the present process may be used for the introduction of a number of carbodiimide groups into a polyisocyanate composition and the product allowed to stand to convert at least a proportion of such groups to uretonimine groups by further reaction. The final products containing a proportion of uretonimine groups are useful as polyisocyanate compositions for the manufacture of polyurethane foams particularly those of the microcellular type often known as microcellular elastomers, having a valuable range of properties.

Refined, i.e. distilled or crystallised, diphenylmethane diisocyanates are solids melting at about 40° C and the process wherein the isocyanate groups are partially converted to carbodiimide groups to the extent of 3% to 35% is particularly valuable with such diphenylmethane diisocyanates as it converts the solid diisocyanate to a liquid composition which is useful in the manufacture of polyurethanes, in particular in that being a liquid it can be incorporated in the polyurethane forming composition without the difficulties inherent in incorporating a low melting solid.

Cyclic phosphorus containing catalysts which may be used in the present process include those of the formulae:

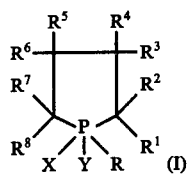 or 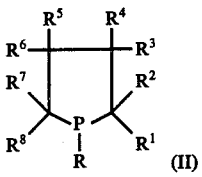

or the 2,3 or 3,4-mono-unsaturated analogues thereof, wherein R is an optionally substituted hydrocarbyl group, $R^1$ to $R^8$ which may be the same or different are hydrogen, chlorine or lower alkyl, X and Y may be chlorine or bromine or X and Y taken together may represent the divalent atoms =O or =S or the divalent radical =N aryl.

By the term lower alkyl used in this specification we mean alkyl having from 1 to 4 carbon atoms.

In referring to the 2,3 and 3,4-mono unsaturated analogues in the above definition of the catalysts it will be appreciated that we are referring to compounds of the formula:

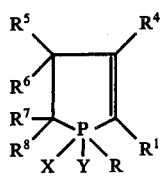

and

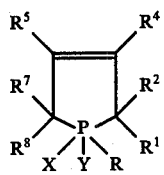

wherein the various R, X and Y groups are as above defined, and also to the related compounds wherein X and Y are absent.

In respect of the catalysts formulated hereinbefore, examples of R include methyl, ethyl, propyl, isopropyl, n-butyl, tert-butyl, cyclohexyl, n-dodecyl, phenyl, o-, m- or p-tolyl, xylyl, naphthyl, 4-diphenyl, 2-phenylethyl, 2-chloroethyl, 2-methoxyethyl, o-, m- or p-chlorophenyl, p-methoxyphenyl and p-N,N-dimethylaminophenyl.

As examples of $R^1$ to $R^8$, which may be the same or may be different, there may be mentioned hydrogen, chlorine, methyl, ethyl, propyl, isopropyl and butyl, a preferred lower alkyl group is methyl.

As examples of X and Y, which may be the same or different, there may be mentioned chlorine and bromine.

As examples of X and Y taken together, there is mentioned the divalent atoms O= and S= and also the divalent radical =N aryl examples of which include phenylimino, p-tolylimino and =N-tolylene-N=V and =N-phenylene-N=V where V is a residue of formula (I) linked through the XY positions.

Specific examples of catalysts which may be used in the present process include:
1-phenyl-3-methyl phospholene oxide
1-benzyl-3-methyl phospholene oxide
1-ethyl-3-methyl phospholene oxide
1-phenyl-3-methyl phospholene dichloride
1-benzyl-3-methyl phospholene dichloride
1-ethyl-3-methyl phospholene dichloride
1-phenyl-3-methyl phospholene sulphide
1-phenyl-3-methyl phospholene sulphide
1-benzyl-3-methyl phospholene sulphide
1-ethyl-3-methyl phospholene sulphide
1-phenyl-1-phenylimino-3-methyl phospholene oxide
1-benzyl-1-phenylimino-3-methyl phospholene oxide
1-ethyl-1-phenylimino-3-methyl phospholene oxide
1-phenyl phospholidine
1-benzyl phospholidine
1-ethyl phospholidine
1-phenyl-3-methyl phospholene oxide.

Preferred catalysts are compounds of Formulae III or IV or mixtures thereof wherein R is phenyl, $R^1$, $R^2$, $R^5$, $R^6$, $R^7$ and $R^8$ are hydrogen, $R^4$ is methyl or chlorine especially methyl and X and Y are as hereinbefore defined. Preferably X and Y together represent a divalent oxygen atom.

A particularly preferred catalyst is 1-phenyl-3-methyl phospholene oxide.

The amount of catalyst used in the process of the invention may vary widely according to the particular catalyst and the desired rate and degree of conversion of the isocyanate groups.

It is a particular feature of this invention that only very small quantities of catalyst are required in this invention. Thus whilst amounts from 1 ppm to as high as 100 ppm may be employed, we find best results to be achieved using considerably less for example less than 25 ppm and preferably less than 10 ppm when an isocyanate having low acidity is employed.

Catalysts for use in the present invention may be made by known methods, thus for example those wherein X and $X^1$ are halogen may be made by direct addition of a dichloride to a 1,3-diene, viz: 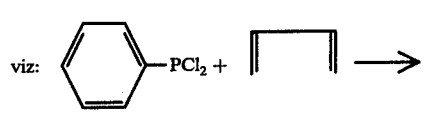

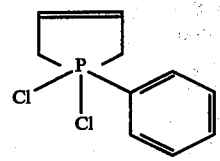

The oxide and sulphide may be made from this chloride by hydrolysis or reaction with sodium sulphide. The phospholenes may be obtained by dehalogenation by reaction with magnesium. Phosphinimines may be prepared by the reaction of phosphines with the appropriate azide.

Isomerisation of the double bond in the ring may take place during these reactions.

Compounds in which the ring is saturated may be conveniently made by adding chloride to the reaction products of, for example, the Grignard reagent from 1,4-dichlorobutane and phenyldichlorophosphine, i.e., ClMg(CH$_2$)$_4$MgCl

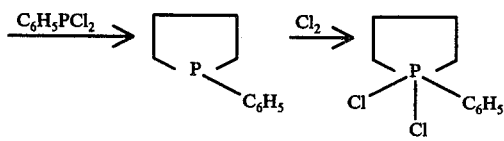

There may also be used as catalyst those cyclic phosphorus compounds described in our copending Applications Nos. 32839/76, 32840/76 and 32841/76.

As nitrogenous bases for use in the present process there may be employed any tertiary amine or its oxide devoid of direct links to aromatic nucleii or guanidines having at least three nitrogen bonded alkyl groups in the molecule. Tertiary amines which have been found to be particularly active include 1,4-diazo bicyclo-[2,2,2]-octane, N,N-dimethyl-cyclo-hexylamine, triethylamine and pyrrolizidine. As examples of guanidines there may be mentioned tetramethyl guanidine and 1,3-dicyclo-hexyl-2-methyl guanidine. As amine oxide there may be used amine oxides of sufficient stability for normal experimental purposes, for example triethylamine oxide.

One particularly preferred tertiary amine is 1,4-diazabicyclo-[2,2,2]-octane.

The amount of base used in the process is best related to the acidity of the isocyanate. Thus amounts of 0.10 to 3.0 moles of nitrogenous base may conveniently be used per mole of acidity in the isocyanate, but amounts outside these limits may be used without deleterious effect.

In carrying out the process of the invention the catalyst and tertiary amine alone or in an organic solvent inert to isocyanates, are added to the isocyanate and the mixture heated to the desired reaction temperature for a length of time sufficient to achieve the desired degree of conversion of isocyanate groups to carbodiimide groups. The time and temperature are clearly interdependent in obtaining a desired degree of conversion. In respect of temperature it is preferred to operate below 150° C in order to minimise side reactions, for example dimerisation which can result in deposition of sediment on storage of the product. A temperature of from 80° C to 140° C has been found convenient and the lower the temperature the lower the rate of dimer formation.

Inert organic solvents which can be used for incorporating the catalyst include chlorinated hydrocarbons such as methylene dichloride, perchloroethylene and monochlorobenzene, and ethers such as dibutyl ether and glycol bis-ethers.

On completion of conversion the reaction mixture is cooled to room temperature and if desired the catalyst may be deactivated.

Deactivation may be carried out by adsorption of the catalyst on a substrate followed by removal of the substrate by physical means or by the addition of one or more of the halides of hydrogen, phosphorus or tin or an oxyhalide of phosphorus or sulphur.

When deactivating the catalyst by the use of a substrate the reaction mixture is treated with a solid adsorbent substrate, optionally after cooling to room temperature.

Solid adsorbent substrates which may be used include siliceous earths and adsorbent carbons.

Specific examples of such substrates include charcoal, activated carbons, silica, alumina, complex silicates such as clays, kieselguhr, bentonite, Fuller's earth and zeolites. Siliceous earths are particularly valuable adsorbents.

Treatment of the reaction mixture with the substrate may be carried out by agitating the substrate in the reaction mixture for a short period of time for example 1 minute to several hours. Treatment may be carried out at any convenient temperature preferably between room temperature and the reaction temperature used to make the product.

Removal of the solid adsorbent substrate from the reaction mixture may be accomplished by decantation, filtration or centrifuging.

Treatment may be effected by a batchwise process or if desired may be effected continuously.

Neither the catalyst nor the substrate interfere with the formation of uretonimine groups by reaction of isocyanate with carbodiimide groups.

When the catalyst is deactivated by the addition of a halide of hydrogen, phosphorus or tin, examples of such deactivators which may be used include hydrogen chloride, hydrogen bromide, phosphorus trichloride, phosphorus pentachloride, tin tetrachloride, tin tetrabromide and tin bromotrichloride.

When the catalyst is deactivated by the addition of an oxyhalide of phosphorus or sulphur, examples of such deactivators include thionyl chloride, sulphuryl chloride and phosphorus pentachloride or oxychloride.

Before adding a chemical deactivator the reaction mixture may be cooled to room temperature but this is not essential.

Chemical deactivators may be used in any convenient amount to provide the deactivating effect. Preferably they are use in an amount of from one to 30 moles of deactivating agent to each mole of catalyst used.

Once deactivation has taken place neither the catalyst not the deactivator are required for, or interfere with, the reaction of carbodiimide groups with isocyanate groups to give uretonimine groups.

Deactivation by adsorption is in general a superior method of deactivation in giving a product of greater thermal stability but chemical deactivation is adequate, simpler and more attractive in that it does not require additional plant items such as separation or filtration apparatus. For this latter reason chemical deactivation is preferred for simplicity of operation.

Thionyl chloride is a preferred deactivator.

In achieving a certain degree of conversion of isocyanate group to carbodiimide groups, conversion can be carried out as hereinbefore described and the conversion stopped by deactivation when the isocyanate group content has dropped to the desired level as determined by known analytical procedures. Alternatively, the conversion can be carried out beyond the desired final level and the product blended with a further amount of the parent isocyanate to give a product having a final total of the desired number of unconverted isocyanate groups. Thus if a product in which 15% of the isocyanate groups have been converted to carbodiimide groups and thence to uretonimine, is required, 20% say of the isocyanate groups can be converted to carbodiimide and the product diluted with further parent isocyanate until the desired product having 85% of the isocyanate group content of the parent isocyanate is obtained. This can simplify the operation in that instead of constantly monitoring the isocyanate group content during conversion, the conversion can be carried on for a given length of time, conversion stopped, the isocyanate content determined and the product diluted to the required isocyanate value.

Compositions made using the present process are more stable to storage at room temperature and are more thermally stable at for example temperatures of up to 80° C.

Products of the present process which contain free isocyanate groups are useful in the manufacture of isocyanate-based polymers such as polyurethanes, isocyanurates and carbodiimides. Thus as a further feature of the present invention there is provided a process for the manufacture of isocyanate-based polymers such as polyurethanes, isocyanurates and carbodiimide polymers wherein the isocyanate starting material is a product containing free isocyanate groups and prepared by the process of the present invention.

Such isocyanate-based polymers may be manufactured by any of the known processes, for example in the case of polyurethanes they may be made by reacting the isocyanate group containing product with compounds containing two or more active hydrogen atoms. The isocyanate-based polymers may be in the form of foamed cellular polymers or elastomers.

The products of the present invention are particularly useful for the manufacture of microcellular polyurethane elastomers and rigid foams containing carbodiimide and isocyanurate residues which are of improved resistance to decomposition at high temperatures. The products of the present invention may also be reacted with a proportion of a glycol or mixture of glycols and the resulting compositions used in the manufacture of polyurethanes.

The invention is illustrated by the following Examples in which all parts and percentages are by weight except where otherwise stated.

EXAMPLE 1

Preparation of di-p-tolylcarbodiimide p-Tolylisocyanate (150 parts) was stirred under a nitrogen atmosphere at 115° C with 2,2,2-diazabicyclo-octane equivalent to the acidity of the isocyanate (0.14 parts) and 1-phenyl-3-methyl-phospholene-1-oxide (0.75 parts of a 0.1% solution in perchloroethylene) an amount of 5 ppm on the isocyanate. After 8 hours, examination by infra-red showed all isocyanate groups to have disappeared. The red-brown single phase liquid was distilled in vacuo to give 96.2 parts (77% of theory) of di-p-tolylcarbodiimide.

When the experiment was repeated using epichlorohydrin in place of 2,2,2-diazobicyclo-octane and using 25 ppm of catalyst, reaction took 24 hours for completion, and the product contained a large amount of solid of melting point above that of di-p-tolylcarbodiimide.

EXAMPLE 2

To 200 parts of methylene bridged polyphenyl-polyisocyanates containing 45% of diphenylmethanediisocyanates and having an average isocyanate functionality of 2.8 and an acidity of 706 ppm, made by phosgenating the mixture of polyarylamines obtained by condensing aniline and formaldehyde in the molar ratio 1.85:1 in the presence of hydrochloric acid was added 5 ppm of 1-phenyl-3-methylphospholene-1-oxide and 1,4-diazabicyclo-[2,2,2]-octane (0.43 parts). After heating for 17 hours at 115° C the isocyanate content of the slightly viscous product was 29.7%.

In a repeat preparation the amount of tertiary amine was doubled and the isocyanate strength was reduced to 26.2% in 2 hours at 115° C.

In a repeat preparation using only 2 ppm of the same phospholene oxide catalyst and 0.86 parts of the tertiary amine the isocyanate content was reduced to 27.05% in two hours.

In the absence of tertiary amine negligble reaction took place. All products were found to absorb at 1370 $cm^{-1}$ on examination by infra red, indicating the presence of uretonimine residues.

EXAMPLE 3

A sample of distilled 4,4'-diisocyanatodiphenyl methane containing 18% of the 2,4'-diisocyanate and having an acidity of 299 ppm was mixed with 2 ppm (0.5 part of a 0.1% w/v solution) of 1-phenyl-3-methylphospholene-1-oxide. Other agents, as tabulated below in an amount equimolar to the acidity of the isocyanate were added and the solution heated to 115° C.

| Agent | Usage for 250 parts of Isocyanate (parts of 10% solution in perchloroethylene) | | Time to isocyanate group content 31% (Minutes) |
|---|---|---|---|
| Triethylphosphite | | 3.39 | 130 |
| Epichlorohydrin | | 1.89 | 90 |
| 2-Methyl-1,3-di-p-tolylisourea | 5.18 | 100 | |
| Epichlorohydrin plus | | 1.89 ⎫ | 70 |
| 2,2,2-diazabicyclo-octane | | 2.29 ⎬ | |
| 2,2,2-diazabicyclo-octane | | 2.29 ⎭ | 70 |
| No agent | | — | No reaction detected in 120 minutes |

EXAMPLE 4

To 250 of just molten diisocyanato-diphenylmethane containing ca 18% of the 2,4'- and 82% of the 4,4'-isomer and having an acidity of 299 ppm measured as hydrogen chloride was added 0.5 ml of a 0.1% w/v solution of 1-phenyl-3-methyl phospholene-1-oxide and 2.29 ml of a 10% w/v solution of 1,4-diazabicyclo[2,2,29 octane in perchloroethylene. The temperature was rapidly raised to 115° C and the fall in isocyanate content was determined with time. After 90 minutes the isocyanate content had fallen to 31.3%. Examination by infra red showed the presence of uretonimine residues (1370 $cm^{-1}$) in the product In an exactly similar way the following results were obtained after 90 minutes reaction:

| Nitrogenous Base | Isocyanate Content (% NCO groups |
|---|---|
| N,N-dimethylaniline | unchanged |
| Triethylamine oxide | 32.2 |
| Tetramethylguanidine | 30.3 |
| Imidazole | 32.6 |
| 1,2-dimethylimidazole | 32.6 |
| 2-Methylimidazole | 31.9 |
| Pyrrolizidine | 31.2 |
| N,N-dimethylcyclohexylamine | 31.2 |
| Triethylamine | 31.1 |

EXAMPLE 5

To 250 parts of 4,4-diisocyanatodiphenylmethane containing acidity of 45 ppm was added at 45° C 1.25 parts of a 0.1% w/v solution of 1-phenyl-3-methyl phospholene-1-oxide and 3.5 parts of a 1% w/v solution of tetramethylguanidine in perchloroethylene. The solution was heated at 115° C for 90 minutes when the isocyanate content had fallen to 27.5%. To 200 parts of this product was added 343 parts of the parent isocyanate to provide a polyisocyanate of isocyanate content 31.2%. To 200 parts of this material there was added 0.03 parts of benzoyl chloride then at 80° C over 1 hour, 9.04 parts of an equimolar blend of 1,2-propylene glycol, 1,3-butylene glycol and diethylene glycol. On cooling to room temperature the product was a very pale straw coloured slightly hazy liquid of good resistance to cooling at low temperatures.

EXAMPLE 6

To 4,000 parts of diisocyanato diphenylmethane containing 18% of the 2,4'-isomer and 81% of the 4,4'-isomer having an acidity of 329 ppm and stabilised against oxidation by addition of ca 330 ppm of triphenyl phosphite and 670 ppm of 2,4-dimethyl-6-(α-methylcyclohexyl) phenol was added 0.8 parts of a 1% w/v solution of 1-phenyl-3-methyl phospholene-1-oxide and also 21.1 parts of a 10% solution of tetramethylguanidine in perchloroethylene. The solution was heated at 110° C for 3 hours when its isocyanate content fell to 31.2%. The product so made was cooled to 80° C, 0.45 parts of benzoyl chloride added then 172 parts of an equimolar blend of 1,2-propylene glycol, 1,3-butylene glycol and diethylene glycol added during one hour at 80° C. The product was a clear orange coloured liquid of isocyanate content 26.2% and viscosity as made of 93.2 centipoise.

EXAMPLE 7

129 Parts of the product of Example 6 were added to 7 parts of a 2:1 w/w blend of trichloro fluoromethane and methylene chloride and 200 parts of a polyol blend.

The polyol blend comprised 70 parts of an oxyethylated oxypropylated diethylene glycol, the oxyethylene tip comprising 20% of the weight of the molecule and of hydroxyl value 30 mg KOH/g and 30 parts of an oxyethylated oxypropylated glycerol having an oxyethylene content of 13%, a hydroxyl value of 32 mg KOH/g and in which 75% of the hydroxyl groups are primary hydroxyls, 15.3 parts of butane diol,1.5 parts of ethylene glycol 2.1 parts of DABCO 33LV, and 0.05 parts of di-n-butyltin di laurate. The resulting mixture began to foam after 13 seconds, foaming was completed after 26 seconds giving a hard microcellular elastomeric material.

EXAMPLE 8

To 1000 parts of a mixture of 80% 2,4- and 20% 2,6-tolylene diisocyanates, of acidity 14 ppm as hydrochloric acid, was added, at 50° C under nitrogen, 0.34 parts of a 10% w/v solution of N,N'-dimethylcyclohexylamine in diethylene glycol dimethyl ether. After 15 minutes stirring 5 ppm (0.5 parts of a 1.0% w/v solution in diethyleneglycol dimethylether) of 1-phenyl-3-methyl phospholene-1-oxide was used.

After 80 minutes at 125° C the isocyanate content had fallen to 36.5% and on cooling 50 ppm (0.5 parts of 10% w/v solution in perchloroethylene) of thionyl chloride was added to the straw coloured product as stabiliser.

EXAMPLE 9

117.5 parts of the product of Example 8 were blended with 30 parts of trichlorofluoromethane and 60.4 parts of a polyol blend comprising:
50 parts of an oxypropylated glycerol having a hydroxyl value of 550 mg KOH/g 7.5 parts of an oxypropylated glycerol having a hydroxyl value of 1120 mg KOH/g
1.5 parts of water
0.4 parts of a polyoxyalkylene polysiloxane surfactant
1 part of N,N'-dimethylcyclohexylamine and the whole mixed for 10 seconds at 2000 rpm and poured into a mould.

A urethane foam containing carbodiimide and uretonimine links was formed.

The foam reached 50% of its total height in 50 seconds.

EXAMPLE 10

350 parts of the product of Example 8 were blended with 20 parts of trichlorofluoromethane and 133.2 parts of a polyol blend comprising 39.9 parts of a glycerol modified polyester based on adipic acid, phthalic anhydride and propylene glycol having a hydroxyl value of 260 mg KOH/g and viscosity 250 poise at 25° C
31.5 parts of an oxypropylated tolylene diamine/triethanolamine (1:1 molar mixture) having a hydroxyl value of 490 mg KOH/g
35 parts of trischloropropyl phosphate
7 parts of a difunctional polyol prepared by condensation of ethylene oxide onto an oxypropylated ethylene glycol
7 parts of a long chain fatty alcohol/ethylene oxide condensate
2.8 parts of a polyoxyalkylene polysiloxane surfactant and
10 parts of a catalyst mixture comprising a 1:1 mixture by weight of potassium 2-ethylhexoate with ethylene glycol containing 5% water, and the whole mixed for 5 seconds at 2000 rpm.
An isocyanurate/urethane foam containing carbodiimide links was formed.

EXAMPLE 11

To 5000 parts of methylene bridged polyphenyl polyisocyanates containing 45% of diphenylmethane diisocyanates and having an average isocyanate functionality of 2.8 and an acidity of 615 ppm, made by phosgenating the mixture of polyarylamines obtained by condensing aniline and formaldehyde in the molar ratio 1.85:1 in the presence of hydrochloric acid, was added separately, at room temperature and under nitrogen atmosphere, 7.5 parts of N,N'-dimethylcyclohexylamine and 20 ppm (1 part 10% w/v solution in perchloroethylene) of 1-phenyl-3-methylphospholene-1-oxide. After heating at 115° C for 80 minutes and cooling, the isocyanate content of the viscous product was 26.1%. On examination by infra red an absorption at 1370 $cm^{-1}$ indicated the presence of uretonimine residues.

EXAMPLE 12

500 parts of the product of Example 11 were blended with 120 parts of trichlorofluoromethane and 190.3 parts of the polyol blend described in Example 10, and the whole mixed for 10 second at 2000 rpm.

An isocyanurate/urethane foam containing uretonimine groups was formed. The foam reached 50% of its total height in 48 seconds. This foam was of very low brittleness compared to a control foam made using a polyisocyanate which had not been uretonimine modified.

EXAMPLE 13

500 parts of the product of Example 11 were blended with 120 parts of trichlorofluoromethane and 32.75 parts of a blend comprising:
- 10 parts of a difunctional polyol prepared by condensation of ethylene oxide onto an oxypropylated ethylene glycol
- 10 parts of a long chain fatty alcohol/ethylene oxide condensate
- 4 parts of a polyoxyalkylene polysiloxane surfactant and
- 8.75 parts of a catalyst mixture comprising a 1:1 mixture by weight of potassium 2-ethylhexoate with ethylene glycol containing 5% water.

An isocyanurate foam containing some uretonimine groups was formed. The foam reached 50% of its total height in 100 seconds.

EXAMPLE 14

235 parts of the product of Example 11 were blended with 60 parts of trichlorofluoromethane and 124.2 parts of a polyol blend comprising:
- 100 parts of an oxypropylated glycerol having a hydroxyl value of 550 mg KOH/g
- 15 parts of an oxypropylated glycerol having a hydroxyl value of 1120 mg KOH/g
- 3 parts of water
- 3.2 parts of a polyoxyalkylene polysiloxane surfactant
- 3 parts of N,N'-dimethylcyclohexylamine and the whole mixed for 10 seconds at 2000 rpm.

A urethane foam containing uretonimine residues was formed. The foam reached 50% of its total height in 120 seconds.

I claim:

1. In a process for the conversion of isocyanate groups to carbodiimide groups which comprises contacting a compound containing isocyanate groups with a cyclic phosphorus compound which catalyses said conversion the improvement which comprises carrying out said conversion in the presence of a nitrogenous base selected from 1,4-diazobicyclo-[2,2,2]-octane, N,N-dimethylcyclohexylamine, triethylamine, pyrrolizidine and tetramethylguanidine.

2. A process as set forth in claim 1 in which said nitrogenous base is 1,4-diazobicyclo-[2,2,2]-octane.

3. A process as set forth in claim 1 in which said nitrogenous base is N,N-dimethylcyclohexylamine.

4. A process as set forth in claim 1 in which said nitrogenous base is triethylamine.

5. A process as set forth in claim 1 in which said nitrogenous base is pyrrolizidine.

6. A process as set forth in claim 1 in which said nitrogenous base is tetramethylguanidine.

* * * * *